United States Patent
Nagasaki et al.

(10) Patent No.: US 10,150,945 B2
(45) Date of Patent: Dec. 11, 2018

(54) CELL CULTURE DEVICE AND MANUFACTURING METHOD THEROF

(75) Inventors: Takeshi Nagasaki, Hyogo (JP); Seiji Shinkai, Fukuoka (JP); Atsushi Uno, Osaka (JP)

(73) Assignees: JNC CORPORATION, Tokyo (JP); TAKESHI NAGASAKI, Hyogo (JP)

( * ) Notice: Subject to any disclaimer, the term of this patent is extended or adjusted under 35 U.S.C. 154(b) by 1671 days.

(21) Appl. No.: 11/187,621

(22) Filed: Jul. 21, 2005

(65) Prior Publication Data

US 2006/0019378 A1 Jan. 26, 2006

(30) Foreign Application Priority Data

Jul. 23, 2004 (JP) ................................. 2004-215747
Feb. 21, 2005 (JP) ................................. 2005-44380
Jul. 14, 2005 (JP) ................................. 2005-205404

(51) Int. Cl.
*C12N 5/00* (2006.01)
*C12M 1/32* (2006.01)

(52) U.S. Cl.
CPC ........ *C12N 5/0068* (2013.01); *C12N 2533/12* (2013.01); *C12N 2533/32* (2013.01)

(58) Field of Classification Search
CPC .............. C12N 5/0068; C12N 2533/12; C12N 2533/32
See application file for complete search history.

(56) References Cited

U.S. PATENT DOCUMENTS

| | | | | |
|---|---|---|---|---|
| 5,674,726 A | * | 10/1997 | Shinto et al. | 435/188 |
| 6,528,514 B1 | * | 3/2003 | Kobayashi et al. | 514/269 |
| 2002/0128234 A1 | * | 9/2002 | Hubbell et al. | 514/100 |
| 2003/0223996 A1 | * | 12/2003 | Ruben et al. | 424/146.1 |

FOREIGN PATENT DOCUMENTS

| | | | | |
|---|---|---|---|---|
| EP | 0599652 | | 6/1994 | |
| JP | 06-181740 | | 7/1994 | |
| JP | 2003171463 A | * | 6/2003 | ............ C08G 69/10 |

OTHER PUBLICATIONS

Machine translation of JP2003-171463 A (translated on Apr. 1, 2011).*
"Laminin-1 peptide-conjugated chitosan membranes as a novel approach for cell engineering¹" Mayumi Mochizuki et al. / The FASEB Journal, vol. 17, May 2003 / p. 875-877.
"Transfection by Polyethyleneimine-Coated Microspheres" William S. Manuel et al. / Journal of Drug Targeting, 2001, vol. 9 No. 1 / pp. 15-22.

* cited by examiner

Primary Examiner — Michael L Hobbs
(74) Attorney, Agent, or Firm — J.C. Patents

(57) ABSTRACT

A low-cost cell culture device with low cytotoxicity and improved cell adhesion is described, manufactured by a simplified coating process. At least the portion for cell culture on the surface of the cell culture device is coated with at least one of ε-poly-L-lysine, further polymerized derivatives of ε-poly-L-lysine and their salts.

12 Claims, 7 Drawing Sheets

1 mg/mL α-Polylysine salt
(160 ng/cm²)

0.2 mg/mL α-Polylysine salt
(130 ng/cm²)

1 mg/mL ε-Polylysine salt
(120 ng/cm²)

0.2 mg/mL ε-Polylysine salt
(100 ng/cm²)

[Fig. 1]
1 mg/mL α-Polylysine salt
(160 ng/cm$^2$)
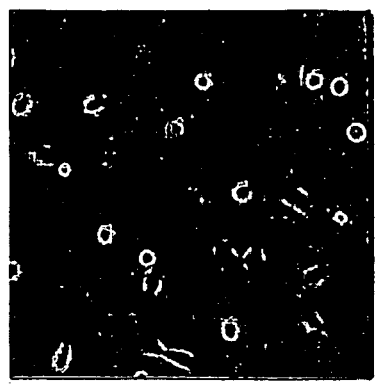
0.2 mg/mL α-Polylysine salt
(130 ng/cm$^2$)
1 mg/mL ε-Polylysine salt
(120 ng/cm$^2$)
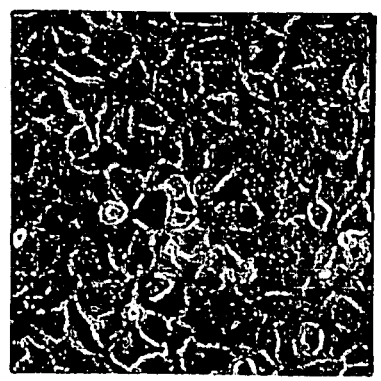
0.2 mg/mL ε-Polylysine salt
(100 ng/cm$^2$)

[Fig. 2]
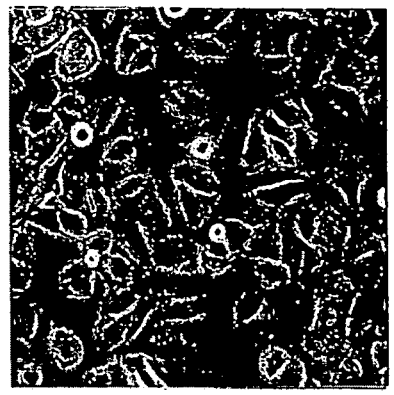
1 mg/mL ε-Polylysine salt
(130 ng/cm$^2$)
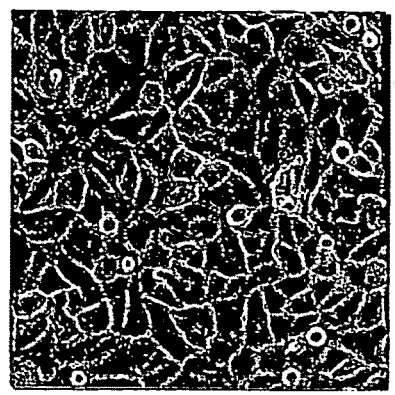
0.2 mg/mL ε-Polylysine salt
(90 ng/cm$^2$)
[Fig. 3]
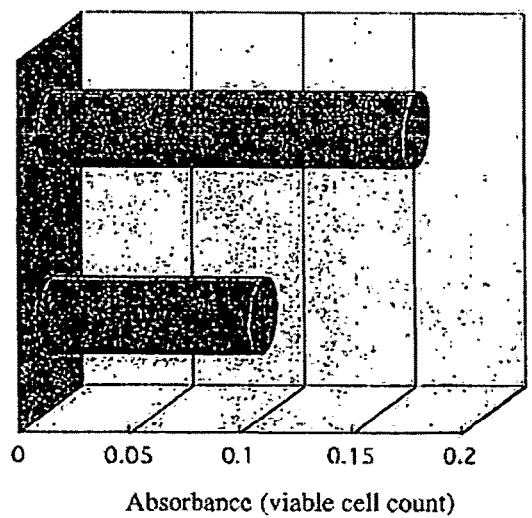
Absorbance (viable cell count)
(upper; epsilon,  lower; alpha)

[Fig. 4]
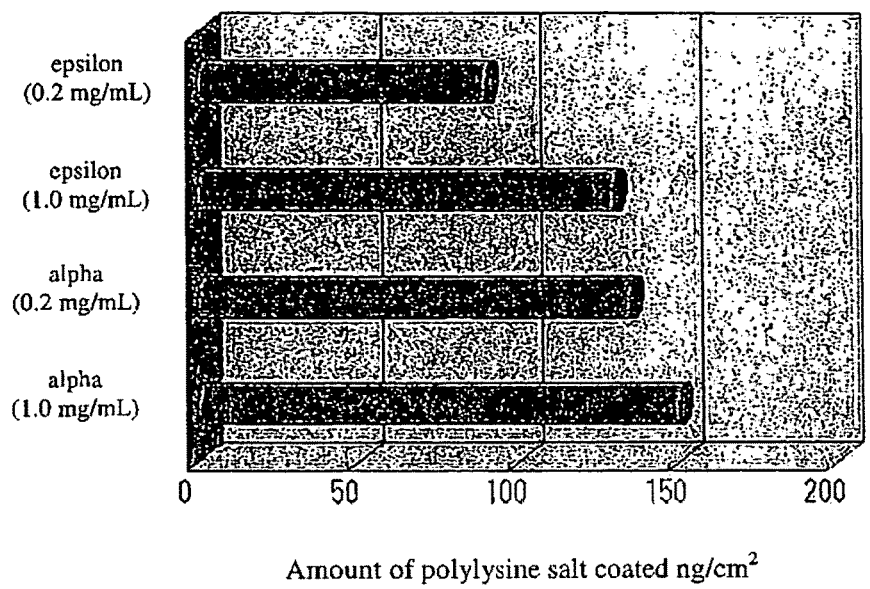
[Fig. 5]
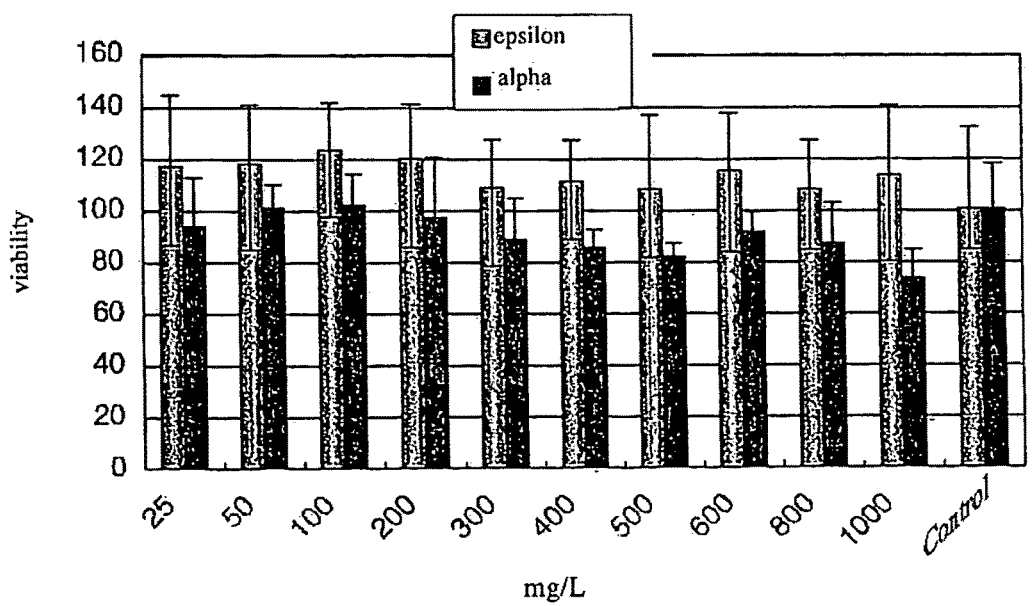

[Fig. 6]
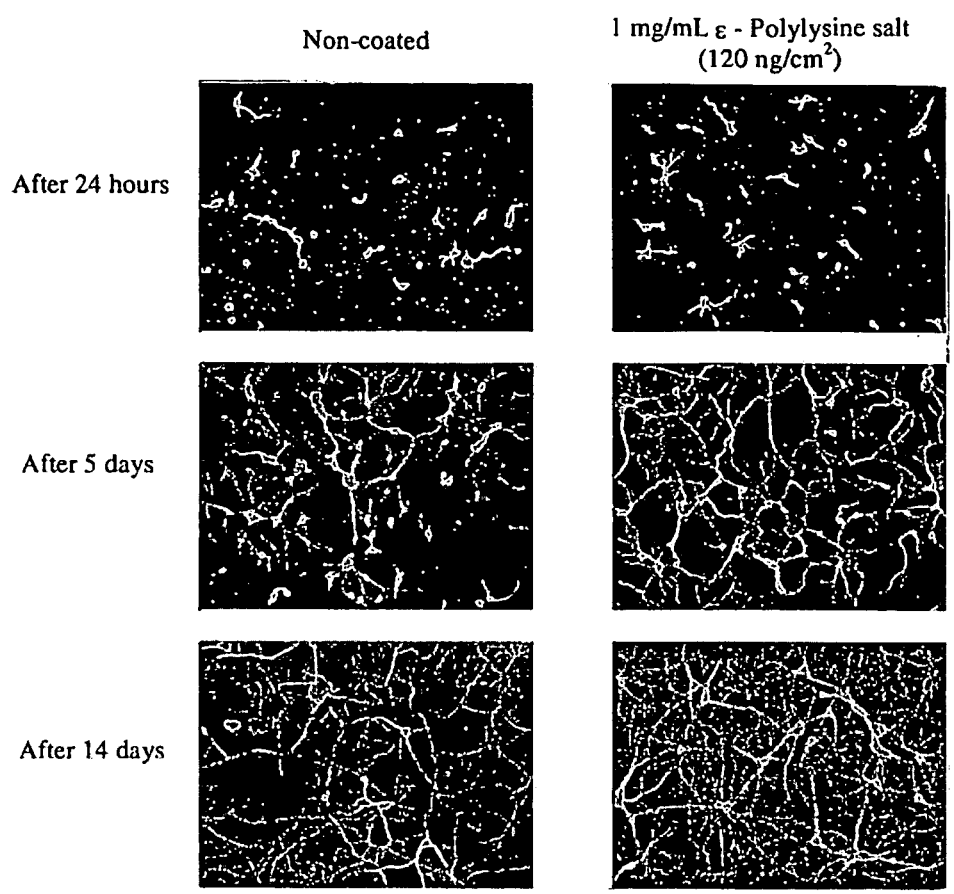

[Fig. 7]
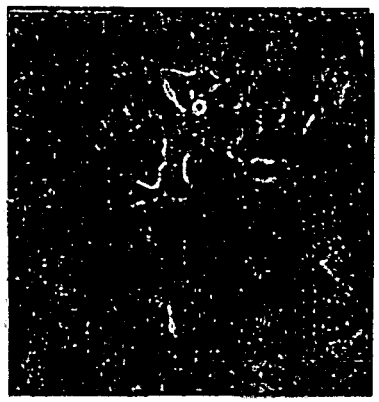
Non-coated
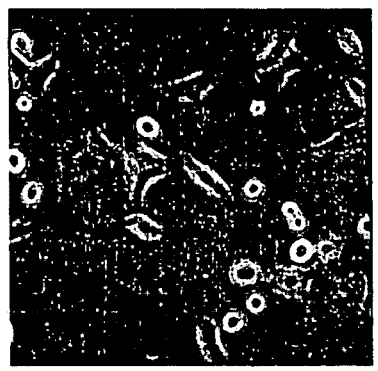
1 mg/mL α - Polylysine salt
(110 ng/cm²)
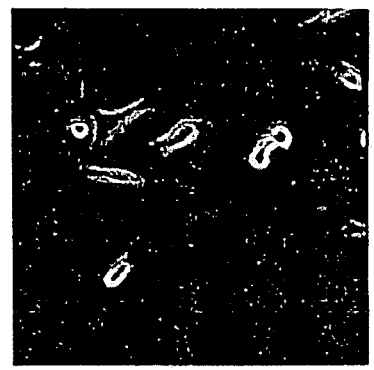
0.2 mg/mL α - Polylysine salt
(50 ng/cm²)
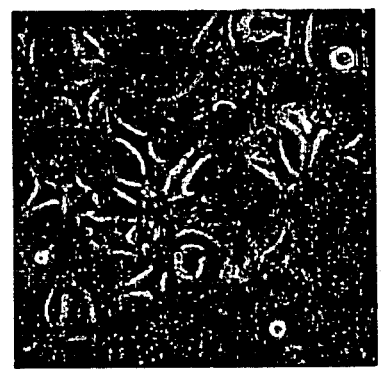
1 mg/mL ε - Polylysine salt
(135 ng/cm²)
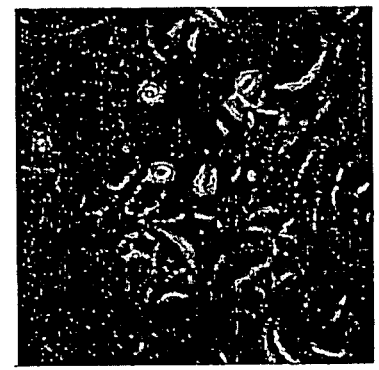
0.2 mg/mL ε - Polylysine salt
(70 ng/cm²)

[Fig. 8]
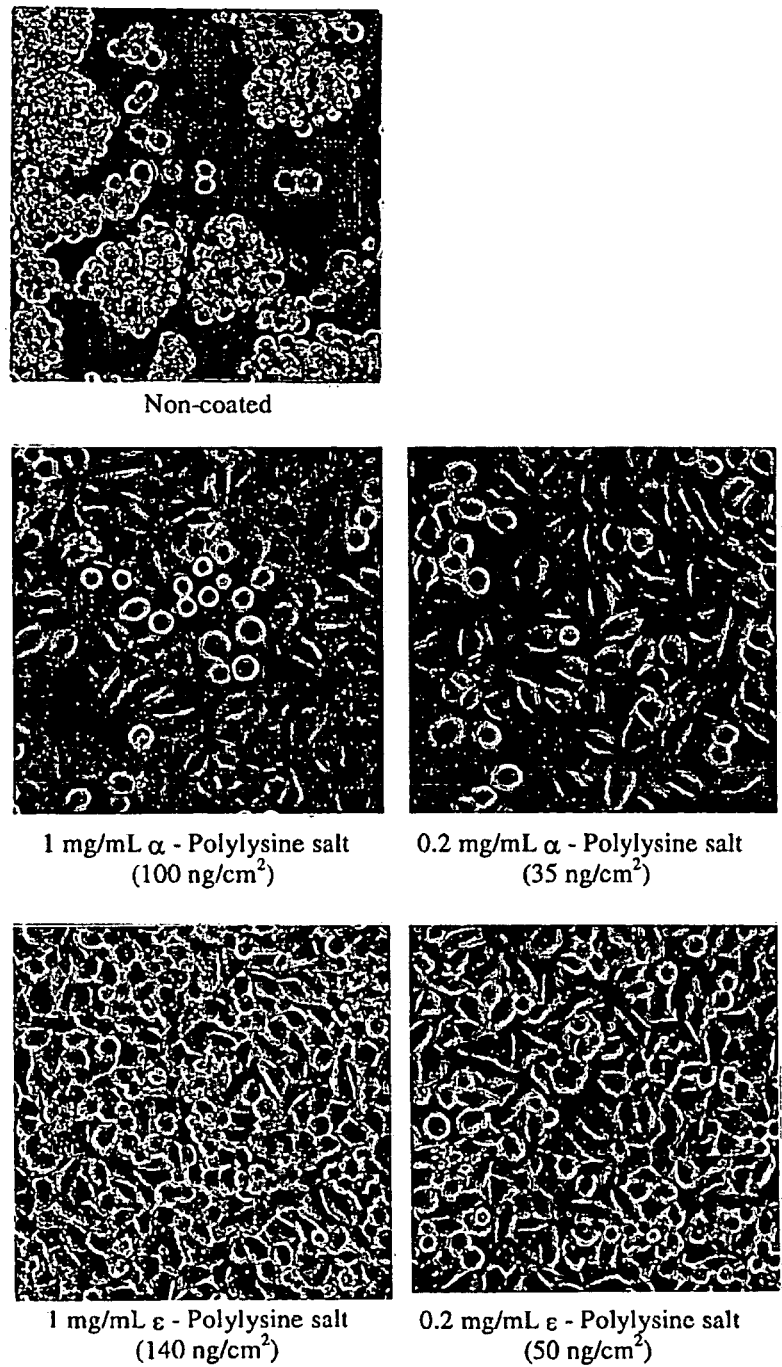

[Fig. 9]
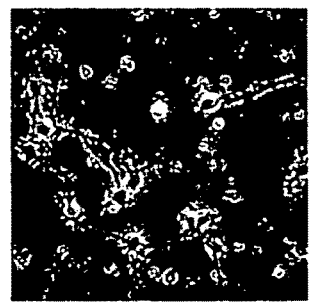
0.05 mg/mL ε-Polylysine salt
($610$ ng/cm$^2$)   (Day 10)
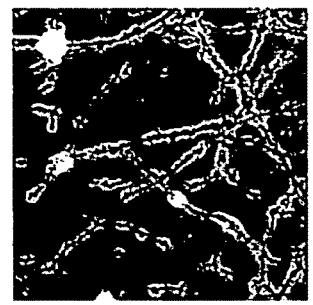
0.05 mg/mL ε-Polylysine salt
($610$ ng/cm$^2$)   (Day 20)
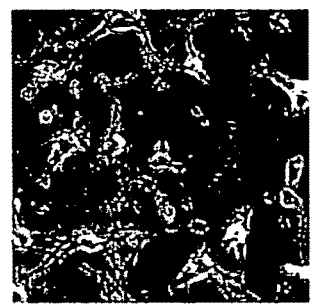
0.2 mg/mL ε-Polylysine salt
($920$ ng/cm$^2$)   (Day 10)
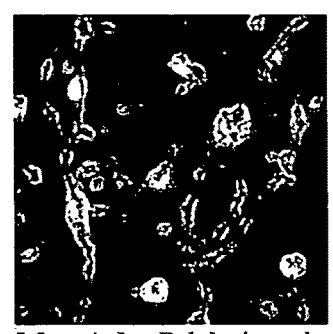
0.2 mg/mL ε-Polylysine salt
($920$ ng/cm$^2$)   (Day 20)
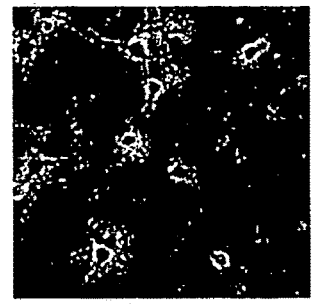
0.05 mg/mL Polymerized ε-Polylysine
($130$ ng/cm$^2$)   (Day 10)
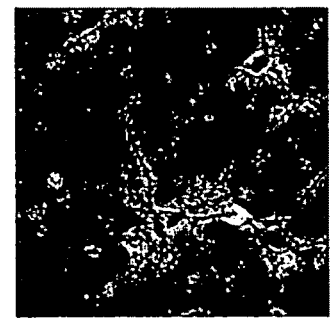
0.05 mg/mL Polymerized ε-Polylysine
($130$ ng/cm$^2$)   (Day 20)
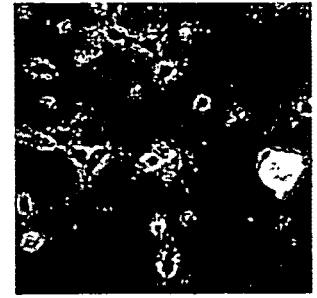
0.2 mg/mL Polymerized ε-Polylysine
($140$ ng/cm$^2$)   (Day 10)
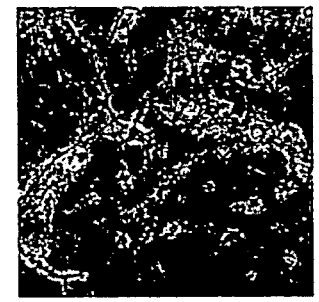
0.2 mg/mL Polymerized ε-Polylysine
($140$ ng/cm$^2$)   (Day 20)

CELL CULTURE DEVICE AND MANUFACTURING METHOD THEROF

BACKGROUND OF THE INVENTION

1. Field of the Invention

The invention relates to a cell culture device the culture surface of which is coated with at least one of ε-poly-L-lysine, further polymerized derivatives of ε-poly-L-lysine and their salts.

2. Technical Background

Devices for the culture of adhesive cells including Petri dishes and chambers, the culture surface of which is coated with a cationic polymer such as α-polylysine or polyethylenimine, to enhance cell adhesion, are generally known (as disclosed e.g. in Patent Ref. 1) and commercially available. Coating materials with higher biocompatibility, such as chitosan, are also under development. Such devices are relatively inexpensive and easy to manufacture, such that they are widely used for primary culture and subculture of adhesive cells, including fibroblasts, smooth muscle cells, blood vessel endothelial cells and corneal cells, as well as floating cells such as blood cells.

However, cationic polymers such as α-polylysine or polyethylenimine are known to have a relatively high cytotoxicity. In addition, although some kinds of cells can grow on such a device, insufficient adhesion or poor development of the cytoskeleton are often observed, particularly in primary cultures. In order to improve adhesion and growth, some commercially available cell culture devices have the culture surface coated with extracellular matrices such as collagen or gelatin, or with biomaterials such as fibronectin, laminin or vitronectin (see e.g. general Ref. 1).

These biomaterials are, however, generally expensive and their method of coating involves cumbersome processes. The stability of the coated surface is also unsatisfactory, presenting problems during storage. An improved culture method is therefore much needed allowing the simple and inexpensive coating of a cell culture surface that possesses low cytotoxicity and which also exhibits effective cell expansion and growth, as well as offering favorable cell morphology and arrangement.

The above Patent Reference 1 is JP-A-H06-181740, and General Reference 1 is Mochizuki, M., Kadoya, Y., Wakabayashi, Y., Kato, K., Okazaki, I., Yamada, M., Sato, T., Sakairi, N., Nishi, N., and Nomizu, M., *FASEB J.*, 17, 875-877 (2003).

SUMMARY OF THE INVENTION

The purpose of this invention is to provide a low-cost cell culture device, with a low cytotoxicity and improved cell adhesion, manufactured by a simplified coating process.

Studies indicated that replacing the α-bonded polylysine conventionally used in the surface coating of the device by at least one of ε-poly-L-lysine, further polymerized derivatives of ε-poly-L-lysine and their salts, in which the amino group at the ε position of lysine is bonded to the carboxyl group, produces a coating which is eminently cationic but has a low cytotoxicity and provides favorable conditions for the adhesion and growth of cells. This finding is the basis for the present invention.

The invention includes the following items. The $1^{st}$ item is a cell culture device wherein the surface of substrate is coated with at least one of ε-poly-L-lysine, further polymerized derivatives of ε-poly-L-lysine and their salts.

The $2^{nd}$ item is about the device of the $1^{st}$ item, wherein the number average molecular weight of the further polymerized derivatives of ε-poly-L-lysine is in a range 8,000 to 100,000. The $3^{rd}$ item is about the device of the $1^{st}$ item, wherein the amount coated of at least one of ε-poly-L-lysine, further polymerized derivatives of ε-poly-L-lysine and their salts is in a range 1 ng/cm$^2$ to 500 μg/cm$^2$. The $4^{th}$ item is about the device of the $1^{st}$ item, wherein the substrate is glass. The $5^{th}$ item is about the device of the $1^{st}$ item, wherein the substrate is synthetic resin.

The $6^{th}$ item is a method of manufacturing a cell culture device wherein the surface of substrate is coated with at least one of ε-poly-L-lysine, further polymerized derivatives of ε-poly-L-lysine and their salts, including a step wherein the substrate of the device is brought into contact with a solution of ε-poly-L-lysine and/or at least one of its salts.

The $7^{th}$ item is about the method of the $6^{th}$ item, wherein the number average molecular weight of the further polymerized derivatives of ε-poly-L-lysine is in a range 8,000 to 100,000. The $8^{th}$ item is about the method of the $6^{th}$ item, including a step of drying the surface after the contact with a solution of at least one of ε-poly-L-lysine, further polymerized derivatives of ε-poly-L-lysine and their salts. The $9^{th}$ item is about the method of the $6^{th}$ item, including a step of removing an excessive amount of the solution after the contact with a solution of at least one of ε-poly-L-lysine, further polymerized derivatives of ε-poly-L-lysine and their salts. The $10^{th}$ item is about the method of the $6^{th}$ item, including a step of removing an excessive amount of said solution followed by a step of drying the surface, after the contact with a solution of at least one of ε-poly-L-lysine, further polymerized derivatives of ε-poly-L-lysine and their salts. The $11^{th}$ item is about the method of the $6^{th}$ item, wherein a solvent of the solution of at least one of ε-poly-L-lysine, further polymerized derivatives of ε-poly-L-lysine and their salts is a borate buffer solution. The $12^{th}$ item is about the method of the $6^{th}$ item, wherein the substrate of the device is glass. The $13^{th}$ item is about the method of the $6^{th}$ item, wherein the substrate of the device is synthetic resin.

ADVANTAGES OF THE INVENTION

The cell culture device according of the invention provides a high cell adhesion, and conditions favorable to cell expansion and growth of cytoskeleton, as well as a low cytotoxicity, owing to the coating of at least the portion used for cell culture of the surface with at least one of ε-poly-L-lysine, further polymerized derivatives of ε-poly-L-lysine and their salts. The invention also provides a manufacturing process whereby at least one of ε-poly-L-lysine, further polymerized derivatives of ε-poly-L-lysine and their salts may be coated in a simple conventional process onto the substrate surface of the device, facilitating a reduction in cost and extensive supply of the device.

BRIEF DESCRIPTION OF THE DRAWINGS

FIG. 1 shows an A549 cell culture on a cell culture device according to the invention (non-dried glass).

FIG. 2 shows another A549 cell culture on a cell culture device according to the invention (dried glass).

FIG. 3 shows the evaluation of viable A549 cell counts on a cell culture device coated with polylysine salt.

FIG. 4 shows the amount of polylysine salt absorbed on the cell culture device coated with polylysine salt.

FIG. 5 shows the viability of A549 cells after treatment with polylysine salt solution, evaluated using Cell Counting Kit-8.

FIG. 6 shows a neurocyte culture on a cell culture device according to the invention (non-dried glass).

FIG. 7 shows still another A549 cell culture on a cell culture device according to the invention (plastic dish).

FIG. 8 shows a HeLa D98 cell culture on a cell culture device according to the invention (plastic plate).

FIG. 9 shows a primary neuron culture on a cell culture device according to the invention (dried glass).

DESCRIPTION OF THE PREFERRED EMBODIMENTS

The cell culture device according to the invention possesses a substrate coating of at least one of ε-poly-L-lysine ("ε-polylysine" hereinafter), further polymerized derivatives of ε-poly-L-lysine and their salts. The coating may cover a part of or the whole surface, provided that the portion of the surface used for cell culture is covered.

The substrate of the device may consist of any material provided it possesses no cytotoxicity and is water-resistant and suitable for cell culture. Generally, materials include glasses and synthetic resins; they should preferably be transparent with respect to the wavelengths (visible or UV) used for observation, taking particularly into account application in fluorescent microscopy. Examples of transparent non-glass materials include polystyrenes, polycarbonates, polyesters, TPX resins (methylpentene polymers), and acrylics; those of opaque non-glass materials include polypropylenes, polyethylenes, and ABS resins.

The substrate may have any shape including, as examples, a plate, bead, fiber or porous body.

ε-Polylysine may be manufactured in any appropriate process. For example, it may be chemically synthesized from lysine, but the synthetic process is difficult and the product is very expensive. A practical process is given in JP 1245361, according to which ε-polylysine is separated from the product obtained by culturing *Streptomyces albulus* ssp. *lysinopolymerus*, as described therein, in a medium adjusted to pH 6.8 consisting 5 wt % glucose, 0.5 wt % yeast extract, 1 wt % ammonium sulfate, 0.08 wt % dipotassium hydrogen phosphate, 0.136 wt % potassium dihydrogen phosphate, 0.05 wt % magnesium sulfate heptahydrate, 0.004 wt % zinc sulfate heptahydrate, and 0.03 wt % iron sulfate heptahydrate.

Further polymerized derivatives of ε-polylysine ("polymerized ε-polylysine" hereinafter) are compounds derived from the polymerization of ε-polylysine as a repeating unit. Manufacturing methods of the polymerized ε-polylysine include, for example, treatment with radiation described in Japan patent publication No. 3502879 and treatment with a cross-linking agent described in Japan unexamined patent publication No. 2003-171464.

However, radiation treatment requires costly equipment or apparatus, and the manufacturing process of polymerized ε-polylysine is required to be highly controlled. In comparison, treatment with a cross-linking agent necessitates prolonged times for the polymerization of ε-polylysine, and also requires a number of additional steps including the separation of unreacted materials.

Simplified and straightforward manufacturing methods of polymerized ε-polylysine include, for example, the method described in Japan unexamined patent publication No. 2003-171463, wherein ε-polylysine undergoes dehydration-condensation by heat treatment at 150° C. or higher in an inert gas or vacuum. In the method, the resultant average molecular weight of polymerized ε-polylysine can be controlled by adjusting the temperature and/or time of treatment, with both the higher temperature and the longer treatment times resulting in higher average molecular weight. The polymerized ε-polylysine manufactured in such methods tends to possess a broader molecular weight distribution and thus appropriate fractionation methods including gel filtration in order to obtain a fraction with the desired molecular weight.

In addition, polymerized ε-polylysine used in the invention may have a wide range of number average molecular weight, while the molecular weight 8,000 to 100,000 is preferable for stable manufacturing. In the invention, molecular weights of ε-polylysine, polymerized ε-polylysine and their salts are determined by SDS-polyacrylamide gel electrophoresis.

Examples of the ε-polylysine or polymerized ε-polylysine salts used in the invention include: inorganic salts formed by reacting ε-polylysine or polymerized ε-polylysine with inorganic acids such as hydrochloric acid, hydrobromic acid, sulfuric acid, or phosphoric acid; organic salts formed by reacting ε-polylysine or polymerized ε-polylysine with organic acids such as acetic acid, formic acid, propionic acid, fumaric acid, malic acid, citric acid, maleic acid, adipic acid, gluconic acid, or lactic acid; saturated fatty acid salts formed by reacting ε-polylysine or polymerized ε-polylysine with medium- or long-chain saturated fatty acids such as capric acid, lauric acid, or stearic acid; and unsaturated fatty acid salts formed by reacting ε-polylysine or polymerized ε-polylysine with medium- or long-chain unsaturated fatty acids such as oleic acid, linoleic acid, or arachidonic acid.

The amount of at least one of ε-polylysine, polymerized ε-polylysine and their salts (sometimes refered to simply as "ε-polylysines" hereinafter) used in coating of the substrate surface should preferably be 1 ng/cm$^2$-500 µg/cm$^2$, or more desirably 5 ng/cm$^2$-5 µg/cm$^2$, or still more desirably 10-500 ng/cm$^2$. These amounts of the coating material ensure suitable conditions for culture of adhesive cells.

The cell culture device according to the invention may be used for primary culture or subculture of any cells, including adhesive cells such as fibroblasts, smooth muscle cells, blood vessel endothelial cells, corneal cells, chondrocytes, hepatocytes, small intestine epithelial cells, epidermal keratosic cells, osteoblasts, medullary mesenchymal cells, embryonic stem cells, adult stem cells, neuroblasts and neurocytes, and floating cells such as blood cells.

Normally a cell suspension and a liquid culture medium (e.g. DME, D-MEM, MEM, HamF12, or HamF10 medium) are applied to the culture surface of the device. Culture conditions suitable for particular cells can be selected.

The manufacturing process of the cell culture device of the invention involves a step that brings the culture surface into contact with an ε-polylysine solution.

Any solvent may be used to prepare the ε-polylysine solution provided it dissolves the substance without any alteration. Examples of the solvent include water, methanol, ethanol-water mixture, isopropanol-water mixture, phosphate buffer solution, borate buffer solution, or a mixture thereof. A borate buffer solution is particularly preferable for coating onto glass.

A method of contacting the culture surface of the device of the invention with the ε-polylysines solution includes spin coating, bar coating or any other known coating process wherein the amount of the solution applied on the area is controlled. Although no drying process is required before the start of cell culture, a drying step at room temperature (23° C.) to 150° C., according to the material composition of the substrate, may be included.

A surface possessing a small culture area or complex geometrical shape that does not lend to uniform coating in a conventional process may be coated by dipping in the ε-polylysines solution or by dropping the solution onto the area.

Although no a priori limit exists for the concentration of the solution, to ensure a sufficient amount of ε-polylysines available and to avoid possible effects of excessive ε-polylysines on the cells cultured, the concentration should preferably be 1.0 ng/mL-20.0 mg/mL, or more desirably 1.0 μg/mL-10.0 mg/mL, or still more desirably, taking the solution cost and amount coated into consideration, 0.01-5.0 mg/mL.

The contact period of the ε-polylysines solution with the substrate surface may be selected as necessary; dipping for several minutes to several tens of minutes will suffice if the contact angle between the solution and the surface is 40 degrees or lower, while contact for a few hours is preferable if the contact angle exceeds 40 degrees. Contact for 12-24 hours is recommended for the culture of cells with poor adhesion.

For the purpose of the invention, it is desirable to control the amount of the ε-polylysines solution applied on the substrate surface by removing excessive solution after the contact process. The excessive solution may be removed by washing the surface after the contact process. The washing medium is normally the same solvent as was used to prepare the ε-polylysines solution, but sterilized water or ultrapure water may also be used. Although no drying process is needed before the start of cell culture, a drying step at room temperature (23° C.) to 150° C., according to the material composition of the substrate, may be included.

EXAMPLES

The invention will be described in further details below using a series of examples, without limiting the scope of the invention, of the manufacture of cell culture devices involving ε-polylysines solution.

Example 1

Manufacture of Coated Cover Glass:

Two ε-polylysine solutions at concentrations of 0.2 mg/mL and 1.0 mg/mL were prepared by dissolving ε-polylysine hydrochloride (hydrochloride salt of ε-polylysine possessing a number average molecular weight of 4,000; manufactured by Chisso Corp.) in 0.1 M borate buffer solution. One day preceding culture experiment, sheets of cover glasses (18 mm, manufactured by Iwaki Glass) were placed in a 10 cm plastic Petri dish, to which 100% ethanol was added. The cover glass sheets were left to stand for 30 minutes at room temperature (23° C.) before being washed two times with ultrapure water (shaken for 10 minutes each time), and subsequently left to stand overnight at 23° C. in 2 mL of the ε-polylysine hydrochloride solution described above. The cover glass sheets were washed two times (shaken for 2 hours each time) with sterilized water on the day of the culture experiment.

Quantification of the Coated ε-Polylysine:

A sheet of the coated cover glass manufactured above was crushed and transferred to a glass tube. The container used in crushing was thoroughly washed with 6 M HCl with 100 μL of 0.1% PhOH to ensure complete transfer. The glass tube was then centrifuged using a centrifuge with a swing-out rotor for 5 minutes at 2000 rpm before being sealed.

The sealed glass tube was then heated in a dry sterilizer for acid hydrolysis: the temperature was raised to 120° C. in 30 minutes and held at that temperature for 5 minutes, then further heated to 150° C. in 20 minutes and held at the temperature for 2 hours. After being cooled down to room temperature (23° C.) the glass tube was opened to transfer the solution contained therein to an Eppendorf tube with filter (Millipore Ultrafree-MC 0.1-μm filter unit) using a Gilson Pipetman, the tube being thoroughly washed with 50 μL of sterilized ultrapure water for complete transfer. The Eppendorf tube then underwent centrifuging for 5 minutes at 2000 rpm and filtration. Lysine in the filtrate was quantified by an amino acid analyzer. The amount of polylysine salt applied on the cell culture surface was determined dividing the amount of polylysine salt calculated from the amount of the lysine by the surface area of the cover glass. The result showed that the amount of ε-polylysine hydrochloride applied on the cell culture surface was 100 ng/cm$^2$ when the 0.2 mg/mL solution was used for coating, and 120 ng/cm$^2$ when the 1.0 mg/mL solution was used.

Comparative Example 1

Coated cover glass sheets were manufactured as in Example 1 except that α-polylysine hydrobromide (Wako Pure Chemical, number average molecular weight 15,000) was used instead of ε-polylysine hydrochloride. Analysis demonstrated that the amount of α-polylysine hydrobromide applied on the cell culture surface was 130 ng/cm$^2$ and 160 ng/cm$^2$, respectively.

Cell Culture Experiment (1)

Coated cover glass sheets manufactured as in Example 1 and Comparative Example 1 were placed in 3.5 cm plastic Petri dishes, to which 1 mL each of DME culture medium (containing 10% bovine embryonic serum) for A549 cells (human lung cancer cells, obtained from ATCC) was added. Then 1 mL each of A549 cell suspension ($1\times10^5$ cells/well) was gradually added onto the cover glass. The cells were examined after 20 hours for adhesion and growth under a phase-contrast microscope. The micrographs shown in FIG. 1 clearly indicate higher adhesion and better expansion of the cells for Example 1 (ε-polylysines coating) than Comparative Example 1, demonstrating that the former is more favorable for cytoskeleton formation.

Example 2

Manufacture of Dry Coated Cover Glass:

Two ε-polylysine solutions at concentrations of 0.2 mg/mL and 1.0 mg/mL were prepared by dissolving ε-polylysine hydrochloride (hydrochloride salt of ε-polylysine possessing a number average molecular weight of 4,000; manufactured by Chisso Corp.) in 0.1 M borate buffer solution. Sheets of cover glasses (18 mm, manufactured by Iwaki Glass) were placed in a 10 cm plastic Petri dish, to which 100% ethanol was added. The cover glass sheets were left to stand for 30 minutes at room temperature (23° C.) before being washed two times with ultrapure water (shaken for 10 minutes each time), and subsequently left to stand overnight at 23° C. in 2 mL of the ε-polylysine hydrochloride solution described above. The cover glass sheets were washed two times (shaken for 2 hours each time) with sterilized water before being completely dried by heating in a dry sterilizer to 70° C. for 12 hours. The amount of applied ε-polylysine hydrochloride was determined as in Example 1.

The amount of ε-polylysine hydrochloride applied on the cell culture surface was 90 ng/cm² and 130 ng/cm², respectively.

Comparative Example 2

Dry coated cover glass sheets were manufactured as in Example 2 except that α-polylysine hydrobromide (Wako Pure Chemical, number average molecular weight 15,000) was used instead of ε-polylysine hydrochloride. Analysis demonstrated that the amount of α-polylysine hydrobromide applied on the cell culture surface was 135 ng/cm² and 150 ng/cm², respectively.

The amounts applied on the cover glass sheets manufactured in Example 2 and Comparative Example 2 are compared in FIG. 4. The amount per unit area is lower for ε-polylysine hydrochloride than for the comparison. This result suggests that the high cell adhesion and low cytotoxicity of ε-polylysines contribute to a coating showing enhanced cell adhesion of the device of the invention.

Cell Culture Experiment (2)

Dry coated cover glass sheets manufactured as in Example 2 were, as in the cell culture experiment (1), placed in 3.5 cm plastic Petri dishes, to which 1 mL each of DME culture medium (containing 10% bovine embryonic serum) for A549 cells was added. Then 1 mL each of A549 cell suspension (1×10⁵ cells/well) was gradually added onto the cover glass. The cells were examined after 20 hours for adhesion and growth under a phase-contrast microscope. The micrographs shown in FIG. 2 indicate that the drying step does not affect the performance of the device according to the invention coated with ε-polylysines.

Determination of Adhered Cell Count:

Dry coated cover glass sheets manufactured in Example 2 and Comparative Example 2 (treated with 0.2 mg/mL polylysine salt solution, amount coated 90 ng/cm² and 135 ng/cm²) were, as in the cell culture experiment (1), placed in 3.5 cm plastic Petri dishes, to which 1 mL each of DME culture medium (containing 10% bovine embryonic serum) for A549 cells was added. Then 1 mL each of A549 cell suspension (1×10⁵ cells/well) was gradually added onto the cover glass.

After culturing for 20 hours, the cells were washed twice with 1 mL of 1×PBS. The cover glass was then carefully lifted off from the Petri dish, avoiding any scratch on the surface, rinsed with 1 mL of 1×PBS, and placed in a two-well culture chamber (Nunc Lab-Tek Chamber Slide 177380), to which 1.1 mL of new medium was added. Then 300 μL each of Cell Counting Kit-8 (Dojindo Laboratories) was added to each well, and the assembly was gently shaken for uniform mixing before being placed in a $CO_2$ incubator to culture for 2 hours at 37° C. 110 μL/well of the culture medium colored by the reaction with Cell Counting Kit-8 was transferred from the chamber to a 96-well plate. A plate reader (Thermo Labsystems Multiskan Ascent BIF) was used to measure absorbance at 450 nm and 620 nm and determine the viable cell count. The results shown in FIG. 3 clearly demonstrate that the cell culture device coated with ε-polylysines ("epsilon") according to Example 2 provides better cell adhesion than one coated with α-polylisine hydrobromide ("alpha") according to Comparative Example 2.

Evaluation of the Cytotoxicity of ε-Polylysines:

The cytotoxicity of ε-polylysines, the coating material used in the invention, to A549 cells (human lung cancer cells, obtained from ATCC) was evaluated. The cytotoxicity to ε-polylysine hydrochloride (Chisso Corp.) was compared with that to α-polylysine hydrobromide (Wako Pure Chemical, average molecular weight 15,000).

A549 cells were seeded on a 96-well microplate at a density of 1×10⁴ cells/well. After culturing overnight at 37° C. under 5% $CO_2$ using DME medium (containing 10% bovine embryonic serum), the medium was removed with an aspirator, and 40 μL each of fresh medium 1.25 times more concentrated as standard was added to each well. Finally 10 μL each of a polylysine salt solution that would eventually attain the specified concentration, and cultured at 37° C. for 3 hours.

After the 3-hour culture, the medium was removed again by an aspirator, 100 μL/well of fresh medium was added, and culture continued for 46 hours. The medium was still once more replaced by 110 μL of fresh medium, 10 μL each of Cell Counting Kit-8 (Dojindo Laboratories) was added and continued to be cultured for 2 hours at 37° C. for color reaction. A plate reader (Thermo Labsystems Multiskan Ascent BIF) was used to determine the absorbance at 450 nm (with 650 nm as a reference) and calculate the viability of the cells. Results are shown in FIG. 5. While no difference is observed at low concentrations, the viability of the cells is significantly lower for α-polylysine hydrobromide than for ε-polylysine hydrochloride at concentrations over 300 mg/L, which indicates the lower cytotoxicity of ε-polylysines.

Cell Culture Experiment (3)

Cover glass sheets coated with 120 ng/cm² of ε-polylysine, prepared as in Example 1, together with non-coated cover glass sheets as a reference, were placed in 24-well plates, to which 1 mL/well of a suspension of primary Rat cerebral cortex-derived neurons, containing 2×10⁴ cells/mL, was added. Adhesion of the cells and growth of the axons were observed after 24 hours, 5 days and 14 days. Results shown in FIG. 6 indicate that the ε-polylysine coating provides better cell adhesion and more growth of axons from the cells than non-coated sheets. The ε-polylysines coating according to the invention is thus shown to be suitable for adhesion and culture of primary neurons.

Example 3

Manufacture of Dry Coated Plastic Dishes:

Two ε-polylysine solutions at concentrations of 0.2 mg/mL and 1.0 mg/mL were prepared by dissolving ε-polylysine hydrochloride (hydrochloride salt of ε-polylysine possessing a number average molecular weight of 4,000; manufactured by Chisso Corp.) in 0.1 M borate buffer solution. A 3.5 cm plastic dish (Greiner Bio-One polystyrene Petri dish, contact angle 65-70 degrees) was filled with 100% ethanol and left to stand for 30 minutes at room temperature (23° C.) before being washed with ultrapure water twice (shaken for 10 minutes each time). The dish was then dipped in 2 mL of the ε-polylysine hydrochloride solution and left to stand overnight at room temperature (23° C.). After being washed with sterilized water twice (shaken for 2 hours each time), the dish was placed in a dry sterilizer and completely dried for 12 hours at 70° C. to obtain a coated plastic dish.

Quantification of the Coated ε-Polylysine:

The coating layer was dissolved by adding 6M HCl to the coated dish, covered with sealing tape, and heated in a dry sterilizer for an hour at 70° C. After allowing to cool, the HCl was completely transferred to a glass tube, to which 6M HCl and 20% PhOH solution were added so that 0.1% PhOH solution in 6M HCl is formed in the glass tube. The tube was then sealed using a gas burner, and heated in a dry sterilizer to allow acid hydrolysis: the temperature was raised to 120° C. in 30 minutes and held at that temperature for 5 minutes, then further heated to 150° C. in 20 minutes and held at the temperature for 2 hours. After being cooled down to room temperature (23° C.) the glass tube was opened, and the opening was covered with Parafilm, in which two holes were pierced using an injection needle. The tube was then placed in a desiccator for removal of the HCl under reduced pressure. Amino acids were dissolved by adding 100 µL of 0.02 M HCl. The solution was dripped into an Eppendorf tube with filter (Millipore Ultrafree-MC 0.1-µm filter unit), and the tube was additionally washed with 50 µL of 0.02 M HCl for complete transfer of the solution to the filter. The total amount of HCl used for dissolution was 150 µL. The Eppendorf tube then underwent centrifugation for 5 minutes at 2000 rpm and filtration. Lysine in the filtrate was quantified by an amino acid analyzer. The amount of polylysine salt applied on the cell culture surface was determined dividing the amount of polylysine salt calculated from the amount of the lysine by the surface area of the plastic dish. The result showed that the amount of ε-polylysine hydrochloride applied on the cell culture surface was 70 ng/cm$^2$ when the 0.2 mg/mL solution was used for coating, and 135 ng/cm$^2$ when the 1.0 mg/mL solution was used.

Comparative Example 3

A dry coated plastic dish was manufactured as in Example 3 with the exception that a-polylysine hydrobromide (Wako Pure Chemical, number average molecular weight 15,000) was used instead of ε-polylysine hydrochloride. Analysis demonstrated that the amount of α-polylysine hydrobromide coated was 50 ng/cm$^2$ and 110 ng/cm$^2$, respectively.
Cell Culture Experiment (4)
One milliliter each of DME culture medium (containing 10% bovine embryonic serum) for A549 cells (human lung cancer cells, obtained from ATCC) was added to the dry coated plastic dishes manufactured according to Example 3 and Comparative Example 3 as well as to a non-coated plastic dish as a reference. Then 1 mL each of A549 cell suspension (1×10$^5$ cells/well) was gradually added to the dishes. The cells were examined after 20 hours for adhesion and growth under a phase-contrast microscope. The micrographs shown in FIG. 7 indicate that a dry coated plastic dish prepared with ε-polylysine hydrochloride provides better cell adhesion that facilitates cytoskeleton formation, compared with a non-coated plastic dish and dry coated plastic dish prepared with α-polylysine hydrobromide, thus showing that ε-polylysine hydrochloride coating of the invention is also effective to ensure cell adhesion and culture performance of cell culture devices made of plastics.

Example 4

Manufacture of Dry Coated Plastic Plates:
Two ε-polylysine solutions at concentrations of 0.2 mg/mL and 1.0 mg/mL were prepared by dissolving ε-polylysine hydrochloride (hydrochloride salt of ε-polylysine possessing a number average molecular weight of 4,000; manufactured by Chisso Corp.) in 0.1 M borate buffer solution. A 24-well plastic plate (Falcon non-treated polystyrene plate, contact angle 80-84 degrees) was filled with 100% ethanol and left to stand for 30 minutes at room temperature (23° C.) before being washed with ultrapure water twice (shaken for 10 minutes each time). The plate was then dipped in 1 mL of said ε-polylysine hydrochloride solution and left to stand overnight at room temperature (23° C.). After being washed with sterilized water twice (shaken for 2 hours each time), the plate was placed in a dry sterilizer and completely dried for 12 hours at 70° C. to obtain a coated plastic plate. The amount of ε-polylysine hydrochloride coated, determined as in Example 3, was 50 ng/cm$^2$ and 140 ng/cm$^2$ from 0.2 mg/mL and 1.0 mg/mL of the solution, respectively.

Comparative Example 4

A dry coated plastic plate was manufactured as in Example 4 except that α-polylysine hydrobromide (Wako Pure Chemical, number average molecular weight 15,000) was used instead of ε-polylysine hydrochloride. Analysis demonstrated that the amount of α-polylysine hydrobromide coated was 35 ng/cm$^2$ and 100 ng/cm$^2$ from 0.2 mg/mL and 1.0 mg/mL of the solution, respectively.
Cell Culture Experiment (5)
One milliliter each of a suspension containing 1×10$^5$ HeLa D98 cells (human uterine cancer cells) with DME culture medium (containing 10% bovine embryonic serum) for those cells was added to dry coated plastic plates manufactured as in Example 4 and Comparative Example 4 as well as to a non-coated plastic plate as a control. The cells were examined after 20 hours for adhesion and growth under a phase-contrast microscope. The micrographs shown in FIG. 8 indicate that a dry coated plastic plate prepared with ε-polylysine hydrochloride provides better adhesion of HeLa D98 cells that facilitates cytoskeleton formation, as in the case for A549 cells, compared with a non-coated plastic plate and a dry coated plastic plate prepared with α-polylysine hydrobromide, thus showing that the ε-polylysine hydrochloride coating is also effective to ensure cell adhesion and culture performance of plastic plates.

Example 5

Manufacture of Polymerized ε-Polylysine:
One hundred (100) milligrams of ε-polylysine possessing a number average molecular weight of 4,000 (manufactured by Chisso Corp.) was placed into a glass microtube, and underwent dehydration-condensation in a vacuum at 185° C. for 40 minutes using a glass tube oven (manufactured by Sibata Scientific Technology Ltd., GTO-350-RD). Polymerized ε-polylysine was obtained, and was confirmed to possess a molecular weight 20,000 to 70,000 by SDS-polyacrylamide gel electrophoresis.
Manufacture of Dry Coated Cover Glass:
Two polymerized ε-polylysine solutions at concentrations of 0.05 mg/mL and 0.2 mg/mL were prepared by dissolving polymerized ε-polylysine prepared as in Example 5 in 0.1 M borate buffer solution. Sheets of round cover glasses (12 mm, manufactured by Matsunami Glass Ind., Ltd.) were placed in a 10 cm plastic Petri dish, to which approximately 15 mL of 100% ethanol was added. The cover glass sheets were left to stand for 30 minutes at room temperature (23° C.) before being washed two times with ultrapure water (shaken for 10 minutes each time), and subsequently placed in a 24-well plate (Falcon non-treated polystyrene plate) and left to stand for 20 hours at 23° C. in 1 mL of the polymerized ε-polylysine solution described above. The cover glass sheets were washed two times (shaken for 2 hours each time) with sterilized water before being completely dried by heating in a dry sterilizer to 70° C. for 12 hours. The amount of polymerized ε-polylysine applied was determined as in Example 1, using polymerized ε-polylysine instead of ε-polylysine salt The amount of polymerized ε-polylysine applied on the cell culture surface was 130 ng/cm² and 140 ng/cm², respectively.

Example 6

Dry coated cover glass sheets were manufactured as in Example 5 except that ε-polylysine hydrochloride (hydrochloride salt of ε-polylysine having number average molecular weight 4,000; manufactured by Chisso Corp.) was used instead of the polymerized ε-polylysine. The amount of ε-polylysine hydrochloride applied was determined as in Example 1. The amount of ε-polylysine hydrochloride applied on the cell culture surface was 610 ng/cm² and 920 ng/cm², respectively.
Cell Culture Experiment (6)

One (1) milliliter per well of a suspension of primary Rat cerebral cortex-derived neurons, containing 2×10⁴ cells/mL, was added to dry coated cover glass sheets prepared as in Example 5 and Example 6. Cells were cultured at 37° C., and adhesion of the cultured cells and growth of the axons were observed under a phase-contrast microscope on day 10 and day 20. Results shown in FIG. 9 indicate that the ε-polylysine coating provides better cell adhesion and axon networking than the polymerized ε-polylysine coating on day 10, while the polymerized ε-polylysine coating provides better cell adhesion and axon networking on day 20 in contrast that coating with ε-polylysine hydrochloride. The polymerized ε-polylysine coating is thus shown to be suitable for cell adhesion and axon networking where neurons are cultured for the long term.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

What is claimed is:

1. A cell culture device wherein the surface of substrate is coated with at least one of further polymerized derivatives of ε-poly-L-lysine and salts of further polymerized derivatives of ε-poly-L-lysine, wherein the further polymerized derivatives of ε-poly-L-lysine are derived from dehydration-condensation of ε-poly-L-lysine,
    wherein the amount coated of at least one of further polymerized derivatives of ε-poly-L-lysine and salts of further polymerized derivatives of ε-poly-L-lysine is in a range 10 ng/cm² to 140 ng/cm².

2. The device of claim 1, wherein the number average molecular weight of the further polymerized derivatives of ε-poly-L-lysine is in a range 8,000 to 100,000.

3. The device of claim 1, wherein the substrate is glass.

4. The device of claim 1, wherein the substrate is synthetic resin.

5. A method of manufacturing a cell culture device wherein the surface of substrate is coated with at least one of further polymerized derivatives of ε-poly-L-lysine and salts of further polymerized derivatives of ε-poly-L-lysine, including a step wherein the substrate of the device is brought into contact with a solution of at least one of further polymerized derivatives of ε-poly-L-lysine and salts of further polymerized derivatives of ε-poly-L-lysine, wherein the further polymerized derivatives of ε-poly-L-lysine are derived from dehydration-condensation of ε-poly-L-lysine,
    wherein the amount coated of at least one of further polymerized derivatives of ε-poly-L-lysine and salts of further polymerized derivatives of ε-poly-L-lysine is in a range 10 ng/cm² to 140 ng/cm².

6. The method of claim 5, wherein the number average molecular weight of the further polymerized derivatives of ε-poly-L-lysine is in a range 8,000 to 100,000.

7. The method of claim 5, including a step of drying the surface after the contact with a solution of at least one of further polymerized derivatives of ε-poly-L-lysine and salts of further polymerized derivatives of ε-poly-L-lysine.

8. The method of claim 5, including a step of removing an excessive amount of the solution after the contact with a solution of at least one of further polymerized derivatives of ε-poly-L-lysine and salts of further polymerized derivatives of ε-poly-L-lysine.

9. The method of claim 5, including a step of removing an excessive amount of the solution followed by a step of drying the surface, after the contact with a solution of at least one of further polymerized derivatives of ε-poly-L-lysine and salts of further polymerized derivatives of ε-poly-L-lysine.

10. The method of claim 5, wherein a solvent of the solution of at least one of further polymerized derivatives of ε-poly-L-lysine and salts of further polymerized derivatives of ε-poly-L-lysine is a borate buffer solution.

11. The method of claim 5, wherein the substrate of the device is glass.

12. The method of claim 5, wherein the substrate of the device is synthetic resin.

* * * * *